Dec. 26, 1972 R. E. DANIELSON Plant Pat. 3,280
CHRYSANTHEMUM MORIFOLIUM
Filed March 22, 1971
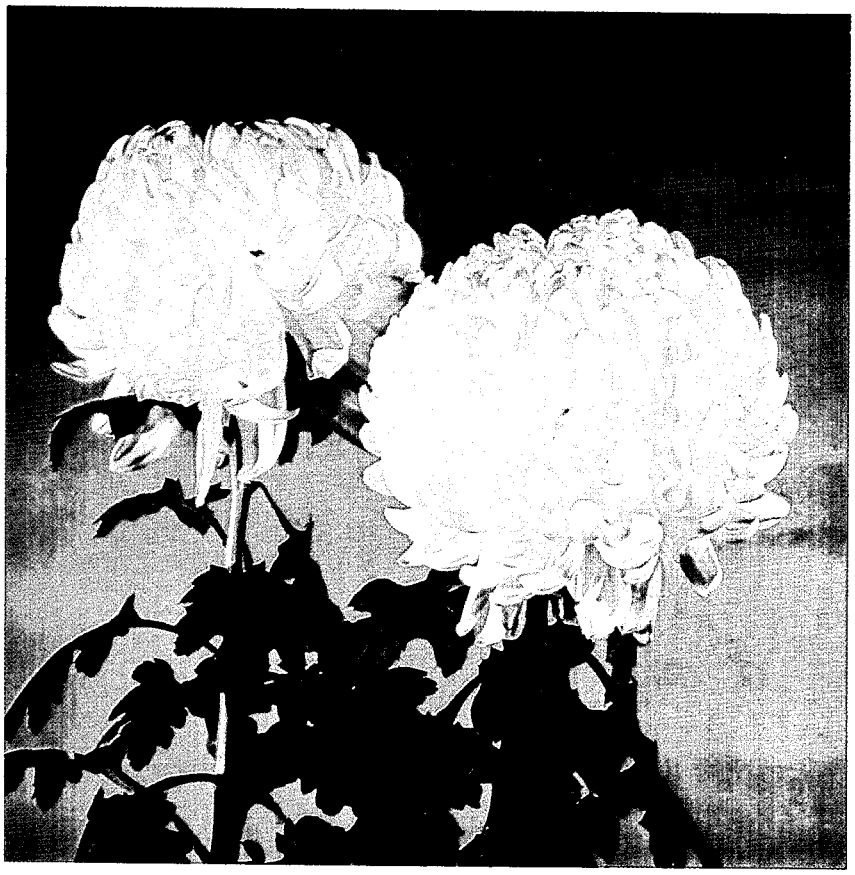
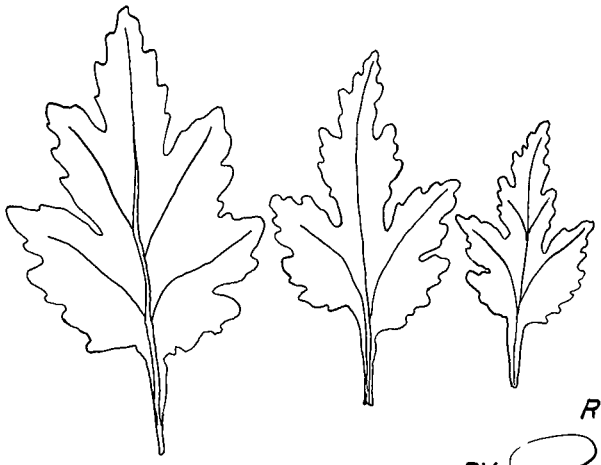
INVENTOR.
ROBERT E. DANIELSON
BY Rummler & Snow
ATTY

United States Patent Office

Plant Pat. 3,280

Patented Dec. 26, 1972

3,280

CHRYSANTHEMUM MORIFOLIUM

Robert E. Danielson, West Chicago, Ill., assignor to Pan-American Plant Company, Chicago, Ill.

Filed Mar. 22, 1971, Ser. No. 127,018

Int. Cl. A01h *5/00*

U.S. Cl. Plt.—78 1 Claim

ABSTRACT OF THE DISCLOSURE

A new variety of chrysanthemum plant originating as a yellow sport of May Shoesmith (unpatented) and characterized by its light yellow coloring, its very large ball-flower type of blooms and its eleven week year-around response to photoperiod culture as a greenhouse plant.

BACKGROUND OF THE NEW PLANT VARIETY

My new variety of chrysanthemum plant resulted from a plant of May Shoesmith (unpatented), which had been irradiated at Chicago, Ill., during September of 1969 and was selected for propagation because of its unusual light yellow coloring and its general retention of the response and growth characteristics of the parent plant. Subsequent flowering and asexual reproduction of the new plant by cuttings and at my direction at West Chicago, Ill., has confirmed the new yellow coloring to be consistent and true. This new variety has also been found to have consistent characteristics of uniform crop production with very few cull flowers, a very high petal count with a typical ball-type of flower, and a response most suited to winter flowering in northern greenhouse culture. For these reasons, the new variety is believed to have high commercial value and is now being propagated by vegetative cuttings and on a commercial scale at West Chicago, Ill.

DESCRIPTION OF THE DRAWING

My new variety of chrysanthemum plant is illustrated by the accompanying drawing which shows typical color characteristics as closely as it is reasonably possible to obtain by conventional photographic procedures, and which shows by pen and ink drawings the configuration and relative sizes of young, intermediate and mature specimens of typical leaves of the new plant.

DESCRIPTION OF THE NEW PLANT

The following is a detailed description of my new variety of chrysanthemum plant with color designations according to the Horticultural Colour Chart of the British Colour Council and as observed on typical plants at West Chicago, Ill., during the winter of 1970–1971.

*The plant*

Origin: Sport.

Parentage: Irradiated May Shoesmith (unpatented). Irradiation done at Chicago, Ill., in September 1969.

Classification: Botanic — *Chrysanthemum morifolium*, Commercial—Standard incurved.

Form: Herbaceous and perennial.

Height: Tall, 2 to 4 feet.

Growth: Vigorous, sturdy and upright with good strength. Branching under natural conditions.

Foliage: Abundant in quantity, with about 27 leaves per 3 feet of stem.

*Leaf size.*—From about 3¼ x 2⅛ inches in the young leaf to about 5½ x 3¾ inches in the mature leaf.

*Shape.*—Broad, cleft and incised.

*Texture.*—Satiny.

*Color.*—Upper side—Spinach Green 0960. Under side—Spinach Green 0960/2.

*Ribs and veins.*—Pinnate.

*Petioles.*—1½ inches long.

*The bud*

Form: Globular, oval in appearance from the side view.

Size: Average—½ inch in diameter and ⅜ inch high.

Opening rate: Slow. 4 weeks to full sized flower.

Color: When sepals first divide—Scheeles Green 860. Color is the same when petals begin to unfurl.

Sepals: Polysepalous—hooded over the bud. Sepals are spear shaped and curl back as petals become fully developed. Color—inside and outside—Scheeles Green 860.

Calyx: Shape—round and flat. Does not split. Aspect—smooth.

Peduncle: Erect and slightly tomentose. Color—Scheeles Green.

*The flower*

Blooming characteristics: Photo responsive for year-around flowering with eleven weak response. Blooms in late November under natural conditions.

Size of bloom: Very large. Approximately 6½ inches in diameter and 4½ inches deep.

Borne: Naturally raceme. Commercially, disbudded to provide one terminal bud.

Shape: Flat and round when bloom first opens. Changes to become more globular as petals develop.

Petalage: Numerous in quantity with capitulum arrangement.

*Form.*—Linear with obtuse apex.

*Color of the flower shown.*—Outer side—Mimosa Yellow 602/2 with Chartreuse Green 663 at base. Inner side—Mimosa Yellow 602/1. The general flower coloring will range from 602 to 602/1 on inner side to 602/1 to 602/2 on outer side of petals.

*Appearance.*—Velvety—slightly tomentose.

Peduncle: Sturdy, erect and upright. About 3 to 4 inches long. Color—Pod Green 061/1.

Effect of weather: Recommended only for greenhouse culture.

Lasting quality: 3 to 4 weeks on the plant. 2 to 3 weeks as a cut flower.

*Reproductive organs*

Stamens: Bloom has 5 syngenesious stamens with anthers connate to form a style.

*Filaments.*—¼ inch long—light yellow in color.

*Pollen color.*—Yellow.

Pistils: One to each ray floret—5/16 inch long.

Stigmas: Color—Yellow.

Ovaries: Inferior thicarpellate.

This new variety of yellow chrysanthemum is very similar to its parent, the white May Shoesmith, in response and growth characteristics and with its eleven-week response, this variety is most suited to winter flowering. It has been grown to flower during the remainder of the year, however, without petal burn. This new variety has very straight and sturdy stems under normal culture, the flower has a very high petal count and when mature has a pleasing and typical ball shape, and very uniform flower crops are produced with remarkably few culls. I know of no other eleven-week yellow chrysanthemum comparable in size and flower form that will produce uniformly during the dark winter months in northern greenhouses.

I claim:

1. A new and distinct variety of chrysanthemum plant, substantially as herein shown and described, particularly characterized by being a yellow bud variation of May Shoesmith.

No references cited.

ROBERT E. BAGWILL, Primary Examiner